United States Patent [19]
Brasier et al.

[11] Patent Number: 5,895,831
[45] Date of Patent: Apr. 20, 1999

[54] SOLID CATALYST ALKYLATION PROCESS

[75] Inventors: Robert S. Brasier, Mount Prospect; Paul A. Sechrist, Des Plaines; Dale J. Shields, Buffalo Grove, all of Ill.

[73] Assignee: UOP LLC, Des Plaines, Ill.

[21] Appl. No.: 08/760,614

[22] Filed: Dec. 4, 1996

[51] Int. Cl.[6] .............. C07C 1/00; C07C 2/56; C07C 2/58

[52] U.S. Cl. .......... 585/711; 585/712; 585/723; 585/729; 585/310; 585/311; 585/314

[58] Field of Search ................. 585/711, 712, 585/723, 729, 310, 311, 314

[56]  References Cited

U.S. PATENT DOCUMENTS

| | | | |
|---|---|---|---|
| 4,009,221 | 2/1977 | Carter | 585/711 |
| 5,382,746 | 1/1995 | Child et al. | 585/724 |

Primary Examiner—Walter D. Griffin
Assistant Examiner—In Suk Bullock
Attorney, Agent, or Firm—Thomas K. McBride; John G. Tolomei; John G. Cutts, Jr.

[57]  ABSTRACT

A process for the production of motor fuel alkylate by reacting an alkene hydrocarbon, an alkane hydrocarbon and a hydrogen halide with a solid alkylation catalyst disposed in swing beds. The spent solid alkylation catalyst is regenerated in a highly integrated flow scheme associated with the alkylate recovery.

11 Claims, 1 Drawing Sheet

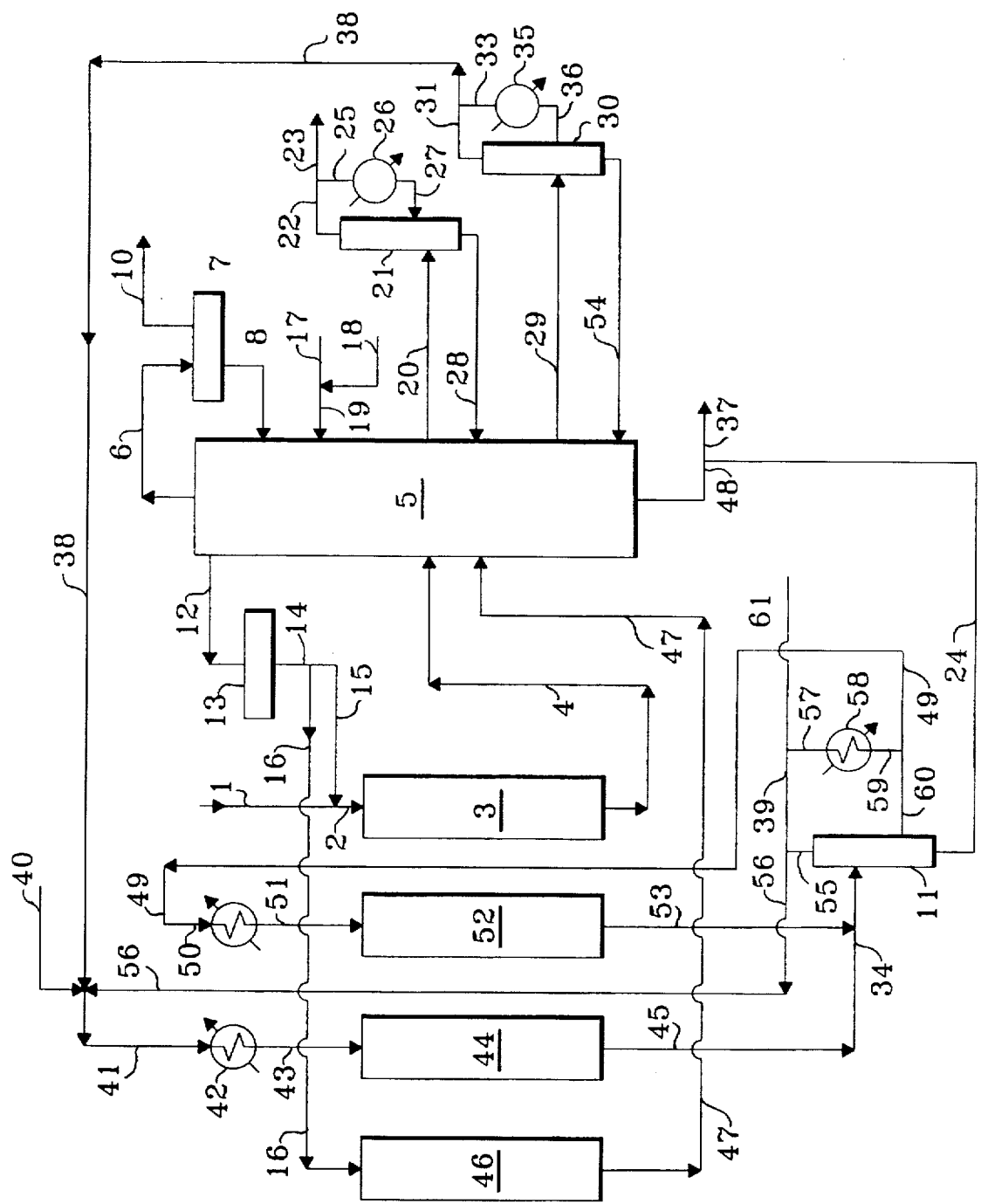

SOLID CATALYST ALKYLATION PROCESS

FIELD OF THE INVENTION

The field of art to which this invention pertains is the production of high octane alkylate by reacting an alkene hydrocarbon and an alkane hydrocarbon in the presence of a solid alkylation catalyst.

BACKGROUND OF THE INVENTION

High octane alkylate is a major blending component of gasoline motor fuel. "Alkylate" generally refers to a mixture of alkanes resulting from the alkylation of $C_2$–$C_6$ olefins (alkenes) with $C_4$–$C_6$ alkanes. It is most desirable that the product mixture, i.e., alkylate, contains predominantly trimethyl pentanes since these are high octane components which add value to gasoline motor fuel. The use of alkylate as a gasoline motor fuel component has become more important owing to government regulations which restrict the use of lead components and butane. In the past, adding lead anti-knock compounds was the easiest way to increase gasoline octane, but because of the deleterious effects of lead emissions, the Environmental Protection Agency (EPA) has mandated the phasing out of the use of lead compounds in gasoline motor fuel. Butane is another effective octane booster, but easily evaporates, especially in warm weather, contributing to smog formation and the resulting atmospheric pollution. The EPA has also required the reduction of butane content of gasoline motor fuel.

The alkylation of olefins by alkanes to give alkylate is a well known reaction and is generally catalyzed by strong acids. Sulfuric acid and liquid hydrofluoric acid (HF) are the commercial catalysts of choice because of their high conversion and selectivity. Of these two catalysts, HF has been favored partly because of the relative ease of HF regeneration.

Recently, hydrofluoric acid (HF) has come under environmental scrutiny owing to its classification as an Acutely Hazardous Material. Furthermore, in southern California the Board of the South Coast Air Quality Management District recently required that the use of HF in alkylation processes be phased out by Jan. 1, 1998. Accordingly, there are incentives for finding substitutes for HF. One such substitute is a solid catalyst which is the reaction product between one or more of the metal halides active as Friedel-Crafts catalysts and a refractory inorganic oxide having surface hydroxyl groups. The refractory inorganic oxide also has dispersed on it a metal having hydrogenation activity for olefins.

One problem associated with solid bed catalysts is that they have limited stability with lifetimes under six hours being common. Attempts at solving this problem have centered on using halides in the feedstream. One such procedure involves using hydrogen halides and/or alkyl halides as the halogen source. However, this results in halogen being present in the product alkylate stream. Accordingly, applicants have developed a solid catalyst alkylation process which effectively removes halides from the product stream in an integrated separation zone and recycles these halides in order to achieve an efficient and economical process.

BRIEF SUMMARY OF THE INVENTION

The present invention relates to a process for the production of motor fuel alkylate by reacting an alkene hydrocarbon, an alkane hydrocarbon and a hydrogen halide at alkylation conditions to produce alkylate.

One embodiment of the present invention may be characterized as an alkylation process for the production of motor fuel alkylate which process comprises: (a) reacting an alkene hydrocarbon, an alkane hydrocarbon and a hydrogen halide at alkylation conditions in a first catalytic reaction zone to produce a hydrocarbon stream comprising alkylate, unreacted alkane hydrocarbon and alkyl halide; (b) separating the hydrocarbon stream comprising alkylate, unreacted alkane hydrocarbon and alkyl halide in a separation zone to produce a hydrocarbon product stream comprising alkylate; (c) introducing an alkane hydrocarbon stream comprising n-alkane hydrocarbon and i-alkane hydrocarbon, and hydrogen halide into the separation zone to produce a stream comprising n-alkane hydrocarbon and a stream comprising i-alkane hydrocarbon and hydrogen halide; (d) passing at least a portion of the stream comprising i-alkane hydrocarbon and hydrogen halide produced in step (c) to step (a) to provide at least a portion of the alkane hydrocarbon; (e) passing n-alkane hydrocarbon to a second catalytic reaction zone to heat and flush the second catalytic reaction zone containing deactivated catalyst in preparation for regeneration of the deactivated catalyst; (f) withdrawing a stream comprising alkane hydrocarbon and alkyl halide from the separation zone and passing at least a portion of the stream comprising alkane hydrocarbon and alkyl halide, and hydrogen to a third catalytic reaction zone containing heated deactivated catalyst to thereby regenerate the heated deactivated catalyst and to produce an effluent stream comprising alkane hydrocarbon and hydrogen halide; and (g) passing at least a portion of the stream comprising i-alkane hydrocarbon and hydrogen halide produced in step (c) to cool and flush a fourth catalytic reaction zone containing newly regenerated catalyst.

Another embodiment of the present invention may be characterized as an alkylation process for the production of motor fuel alkylate which process comprises: (a) reacting an alkene hydrocarbon, an alkane hydrocarbon and a hydrogen halide at alkylation conditions in a first catalytic reaction zone to produce a hydrocarbon stream comprising alkylate, unreacted alkane hydrocarbon and alkyl halide; (b) separating the hydrocarbon stream comprising alkylate, unreacted alkane hydrocarbon and alkyl halide in a first separation zone to produce a hydrocarbon product stream comprising alkylate; (c) introducing an alkane hydrocarbon stream comprising n-alkane hydrocarbon and iso-alkane, and hydrogen halide into the first separation zone to produce a stream comprising n-alkane hydrocarbon and a stream comprising iso-alkane hydrocarbon and hydrogen halide; (d) passing at least a portion of the stream comprising iso-alkane hydrocarbon and hydrogen halide produced in step (c) to step (a) to provide at least a portion of the alkane hydrocarbon; (e) passing n-alkane hydrocarbon to a second catalytic reaction zone to heat and flush the second catalytic reaction zone containing deactivated catalyst in preparation for regeneration of the deactivated catalyst; (f) withdrawing a stream comprising alkane hydrocarbon and alkyl halide from the first separation zone and passing at least a portion of the stream comprising alkane hydrocarbon and alkyl halide, and hydrogen to a third catalytic reaction zone containing heated deactivated catalyst to thereby regenerate the heated deactivated catalyst and to produce an effluent stream comprising alkane hydrocarbon and hydrogen halide; (g) passing at least a portion of the effluent stream comprising alkane hydrocarbon and hydrogen halide from step (f) and at least a portion of the n-alkane effluent from step (e) to a second separation zone to produce a stream comprising n-alkane, and a vapor stream comprising hydrogen and hydrogen halide; (h) passing at least a portion of the stream comprising n-alkane produced in step (g) to step (e) to provide at least a portion of the n-alkane hydrocarbon; (i) passing at least a portion of the vapor stream comprising hydrogen and hydrogen halide produced in step (g) to step (f) to provide at least a portion of the hydrogen; and (j) passing at least a portion of the stream comprising isoalkane hydrocarbon and hydrogen halide produced in step (c) to a fourth catalytic reaction zone containing freshly regenerated catalyst to thereby cool the freshly regenerated catalyst to alkylation temperature.

Other embodiments of the present invention encompass further details such as preferred catalysts and operating conditions.

The process of the present invention provides the advantages of the facile production of motor fuel alkylate without the environmental disadvantages of the prior art alkylation processes.

BRIEF DESCRIPTION OF THE DRAWING

The drawing is a simplified flow diagram of a preferred embodiment of the present invention. The above-described drawing is intended to be schematically illustrative of the present invention and is not intended to be a limitation thereof.

DETAILED DESCRIPTION OF THE INVENTION

The present invention relates to a process for the production of motor fuel alkylate. The alkylate is produced in a reaction zone containing a solid acid catalyst wherein an alkane is reacted with an olefin in the presence of a hydrogen halide. The alkanes which are preferably used are those that contain from 4 to 6 carbon atoms with branched alkanes being most preferred, e.g., isobutane. The olefins (alkenes) which are used are those that have from 3 to 6 carbon atoms and preferably 4 to 5 carbon atoms, e.g., 1-butene, isobutylene, 2-butenes, etc.

The reaction between alkanes, olefins and hydrogen halide to form alkylate is catalyzed by solid acid catalysts. Generally effective catalysts are solid acid catalysts, identified as strong Lewis acids, as well as supported sulfuric and phosphoric acids. Examples of such materials include silica impregnated with sulfuric acid (U.S. Pat. No. 5,336,833), heteropoly acids, as exemplified by heteropolymolybdates and heteropoly tungstates, especially as supported on molecular sieves (see U.S. Pat. No. 5,324,881 for examples of heteropoly acids as well as supports), sulfated zirconia as exemplified in U.S. Pat. No. 5,310,868, various zeolitic materials as summarized in U.S. Pat. No. 5,258,569, supported fluorinated sulfonic acids (U.S. Pat. No. 5,245,100), Lewis acids such as $BF_3$, $SbF_5$, $AlCl_3$, $GaCl_3$, and so forth (U.S. Pat. Nos. 5,245,101; 5,190,904; 5,157,197) either alone or in combination with zeolitic materials (U.S. Pat. No. 5,191,148) or as composites. The Lewis acids based on aluminum, gallium, antimony and boron halides are especially attractive. All of the above-identified references are incorporated by reference.

The reaction conditions for effecting alkylation clearly will depend upon the alkane, olefin and hydrogen halide used as well as the particular catalyst employed. Sufficient pressure is used to ensure a liquid phase reaction, but the pressure is otherwise unimportant as a reaction variable influencing the course of alkylation. Clearly, the pressure necessary to maintain a liquid phase reaction depends upon the reaction temperature as well as the reactant, but pressures in the range of 100–1500 psig (689–10342 kPa gauge) generally will suffice. Alkylation temperatures may be as low as about −40° F. (−40° C.) and as high as about 302° F. (150° C.), depending upon the reactants as well as the particular solid acid catalyst used. For example, for the preferred catalyst described above, temperatures between about 32° F. (0° C.) and about 122° F. (50° C.) generally will suffice and are preferred.

The alkylation reaction is carried out in an alkylation zone as a continuous reaction with the reactants in the liquid phase. The catalytic composite is present either as a fixed bed or a moving bed and the reaction stream containing a mixture of hydrogen halide, olefins and alkanes is flowed either in an upflow or downflow mode over the catalyst. The feedstock generally is flowed over the catalyst at a liquid hourly space velocity of about 0.5 to about 5.0 $hr^{-1}$.

Regardless of how the alkylation is carried out, the product stream from the alkylation zone will contain a mixture of components including hydrogen halides, isobutane, $C_2$–$C_7$+ alkanes, alkyl halides and trace levels of cyclic compounds. This product stream is passed to a first separation zone or isostripper which is operated at conditions necessary to separate the product stream into an overhead stream, a first side stream, a second side stream, a third side stream and a bottom stream. The overhead stream comprises mainly hydrogen halide with small amounts of propane and isobutane. The first side stream comprises mainly isobutane with minor amounts of hydrogen halide and n-butane, while the second side stream contains n-butane. The third side stream contains $C_5$–$C_6$ alkanes as the main component with some n-butane and minor amounts of alkyl halides and, finally, the bottom stream contains $C_7$+ alkanes. In accordance with the present invention, the desired reaction is the alkylation of an alkene hydrocarbon and an alkane hydrocarbon to produce an alkylate. Preferred species of alkanes and alkenes are hydrocarbons containing from 2 to about 6 carbon atoms. These preferred species are identified and used throughout the specification to aid in the description of the present invention.

The operating conditions in the first separation zone include a temperature of about 95° F. (35° C.) to about 464° F. (240° C.) and a pressure of about 689 kPa (100 psig) to about 1724 kPa (250 psig). The bottom stream containing $C_7$+ alkanes or alkylate is collected and blended with other hydrocarbons to give a motor fuel product.

At least a portion of the first side stream from the first separation zone containing isobutane and hydrogen halide is introduced into a first catalytic reaction zone to produce alkylate. The second side stream containing n-butane is preferably introduced into a rectification zone to produce a purified n-butane stream and return a rectification bottom stream to the first separation zone.

A stream containing n-butane is heated and introduced into a second catalytic reaction zone containing spent alkylation catalyst in preparation for the regeneration of the spent catalyst. The spent catalyst is heated to a temperature in the range from about 250° F. (121° C.) to about 500° F. (260° C.). The resulting effluent from the second catalytic reaction zone is introduced into a second separation zone or regenerate stripper to produce an n-butane stream which is subsequently recycled to the second catalytic reaction zone.

The third stream containing $C_5$–$C_6$ alkanes and alkyl halides is preferably purified in a rectification zone. At least a portion of the third side stream containing $C_5$–$C_6$ alkanes and alkyl halides, a make-up hydrogen stream and a gaseous stream containing hydrogen and hydrogen halide is heated to a temperature in the range from about 250° F. to about 500° F. and introduced into a third catalytic reaction zone containing spent catalyst and having been previously heated as described hereinabove in order to regenerate the catalyst. Hydrogen is also present during regeneration in order to convert the alkyl halides to alkanes and hydrogen chloride. The resulting effluent from the third catalytic reaction zone containing hydrogen, hydrogen halide and alkane is introduced into the regenerate stripper to produce a stream containing n-butane and a vapor stream containing hydrogen and hydrogen halide.

At least another portion of the first side stream comprising isobutane and hydrogen halide is introduced into a fourth catalytic reaction zone to cool the newly regenerated catalyst to alkylation temperature. The resulting effluent is then returned to the first separation zone or isostripper.

An alkane feed stream containing both iso and normal compounds and hydrogen chloride is also introduced into the isostripper.

As another option, at least a portion of the second side stream containing n-butane is introduced into an isomerization zone where the n-butane is isomerized to isobutane by contacting the n-butane with an isomerization catalyst at isomerization conditions. Isomerization catalysts and conditions are well known in the art and are described in U.S. Pat. Nos. 2,999,074; 3,652,697; 3,128,319 and 3,112,356, all of which are incorporated by reference. The catalyst is one in which a metal halide of the Friedel-Crafts type is reacted with a refractory metal oxide and the support also has dispersed thereon a platinum group metal. The isomerization conditions include a temperature of about 0° C. to about 500° C. and a pressure of about 101 kPa (14.7 psi) to about 20.265 kPa (2940 psi). The resulting effluent from this isomerization zone is recycled to the first separation zone or isostripper in order to separate the isobutane from unreacted n-butane.

DETAILED DESCRIPTION OF THE DRAWING

In the drawing, the process of the present invention is illustrated by means of a simplified flow diagram in which such details as pumps, instrumentation, heat-exchange and heat-recovery circuits, compressors and similar hardware have been deleted as being non-essential to an understanding of the present invention. The use of such ancillary equipment is well within the purview of one skilled in the art.

With reference now to the drawing, an olefin hydrocarbon feed stream is introduced into the process via conduit 1 and is admixed with an alkane stream containing a hydrogen halide supplied via conduit 15 and the resulting admixture is introduced via conduit 2 into catalytic reaction zone 3. An effluent containing alkylate, unreacted alkane hydrocarbon and alkyl halide is transported via conduit 4 from catalytic reaction zone 3 and introduced into separation zone 5. Saturated hydrocarbons including iso-alkane and n-alkane are introduced into the process via conduits 17 and 19 and passed into separation zone 5. A hydrogen halide is introduced into separation zone 5 via conduits 18 and 19. A stream containing n-alkane and small quantities of alkyl halide is withdrawn from separation zone 5 via conduit 20 and introduced into rectification zone 21. The alkyl halide is removed from rectification zone 21 via conduit 28 and recycled to separation zone 5. A purified n-alkane stream from rectification zone 21 is removed via conduit 22 and at least a portion is carried via conduit 25 into heat exchanger 26 to produce a liquid reflux stream which is returned to rectification zone 21 via conduit 27. Another portion of the n-alkane is removed from the process via conduit 23.

An overhead stream containing $C_3$-minus hydrocarbons and hydrogen halide is removed from separation zone 5 via conduit 6 and collected in overhead receiver 7. A portion of the condensed overhead from overhead receiver 7 is refluxed via conduit 8 to separation zone 5 and another portion is removed from the process via conduit 10.

Another stream containing alkanes, alkyl halides and alkylate is withdrawn from separation zone 5 via conduit 29 and introduced into rectification zone 30. The alkylate is removed from rectification zone 30 via conduit 54 and recycled to separation zone 5. A purified stream containing alkanes and alkyl halide from rectification zone 30 is removed via conduit 31 and at least a portion is carried via conduit 33 into heat exchanger 35 to produce a liquid reflux stream which is returned to rectification zone 30 via conduit 36. Another portion of the alkanes and alkyl halide is transported via conduit 38 and joined with a stream containing $C_3$-minus hydrocarbons and hydrogen halide provided via conduit 56 as described hereinafter. The resulting admixture is transported via conduit 41 and contacted with hydrogen introduced via conduit 40. This resulting admixture is passed via conduit 41 into heat-exchanger 42. The resulting heated effluent from heat-exchanger 42 is introduced via conduit 43 into catalytic reaction zone 44. The resulting effluent from catalytic reaction zone 44 is introduced to separation zone 11 via conduits 45 and 34.

An overhead stream from separation zone 11 is removed via conduit 55 and at least a portion is transported via conduit 56 to supply $C_3$-minus hydrocarbons and hydrogen halide as described hereinabove. Another portion is transported via conduits 55, 39 and 61, and removed from the process. Another portion is transported via conduits 55, 39 and 57 and cooled in heat-exchanger 58. A liquid stream is removed from heat-exchanger 58 via conduit 59 and at least a portion is refluxed to separation zone 11 via conduits 59 and 60. Another portion is transported via conduits 59 and 49 and introduced into heat-exchanger 50. A heated vapor stream is removed from exchanger 50 via conduit 51 and introduced into reaction zone 52. The resulting effluent from reaction zone 52 is removed via conduit 53 and introduced via conduits 53 and 34 into separation zone 11. A stream containing alkylate is removed from separation zone 11 via conduits 24 and 37 and recovered.

A stream containing an alkane and hydrogen halide is removed from separation zone 5 via conduit 12 and introduced into receiver 13. At least a portion of the alkane and hydrogen halide is removed from receiver 13 and transported via conduits 14 and 15 as described hereinabove. Another portion of the alkane and hydrogen halide is removed from receiver 13 and transported via conduits 14 and 16 to catalytic reaction zone 46. The resulting effluent from catalytic reaction zone 46 is recycled to separation zone 5 via conduit 47. An alkylate product stream is removed from separation zone 5 via conduits 48 and 37 and recovered.

The process of the present invention is further demonstrated by the following illustrative embodiment. This illustrative embodiment is, however, not presented to unduly limit the process of this invention, but to further illustrate the advantages of the hereinabove-described embodiment. The following data were not obtained by the actual performance of the present invention, but are considered prospective and reasonably illustrative of the expected performance of the invention.

ILLUSTRATIVE EMBODIMENT

An olefin feed in an amount of 100 mass units per hour is introduced into the process and mixed with an iso-alkane stream containing hydrogen halide in an amount of 874 mass units per hour and introduced into an on-line catalytic reaction zone containing active alkylation catalyst. The resulting effluent from the catalytic reaction zone containing alkylate, unreacted alkane hydrocarbons and alkyl halide is introduced into an isostripper fractionation zone. A stream of saturated hydrocarbons including iso-alkane and n-alkane in an amount of 148 mass units per hour and a stream of hydrogen halide in an amount of 0.5 mass units per hour are introduced into the isostripper fractionation zone. A stream in an amount of 179 mass units per hour containing n-alkane and alkyl halide is withdrawn from the isostripper fractionation zone and introduced into an n-alkane rectification zone. A bottoms stream in an amount of 51 mass units per hour is removed from the n-alkane rectification zone and returned to the isostripper fractionation zone. A net overhead stream containing n-alkane in an amount of 128 mass units per hour is removed from the process and recovered. An overhead stream containing $C_3$-minus hydrocarbons and hydrogen halide in amount of 147 mass units per hour is removed from the isostripper fractionation zone and cooled. A net overhead stream in an amount of 2.4 mass units per hour is removed from the process and recovered with the balance refluxed to the isostripper fractionation zone.

Another stream containing alkanes, alkyl halides and alkylate in an amount of 35 mass units per hour is withdrawn from the isostripper fractionation zone and introduced into a regenerate rectifier. A bottoms stream in an amount of 17 mass units per hour is removed from the regenerate rectifier and returned to the isostripper fractionation zone. A net overhead stream containing alkanes and alkyl halide in an amount of 18 mass units per hour is removed from the regenerate rectifier, admixed with 0.22 mass units per hour of hydrogen and 43 mass units per hour of regenerate stripper overhead product and heated to regeneration temperature. This resulting heated admixture is introduced into an off-line catalytic reaction zone containing spent or deactivated catalyst. The resulting effluent from this off-line catalytic reaction zone is introduced into a regenerate stripper.

A portion of a liquid stream from the overhead of the regenerate stripper in an amount of 144 mass units per hour and containing n-alkane is heated and introduced into an off-line catalytic reaction zone containing spent or deactivated catalyst in preparation for the regeneration step described hereinabove. The resulting effluent from this off-line catalytic reaction zone is also introduced into the regenerate stripper. A gaseous net overhead product in an amount of 1.5 mass units per hour and containing hydrogen and hydrogen halide is removed from the regenerate stripper and recovered.

After the regeneration of an off-line catalytic reaction zone containing regenerated alkylation catalyst, a stream in an amount of 159 mass units per hour and containing iso-alkane and hydrogen halide is passed through the off-line catalytic reaction zone to cool the alkylation catalyst to alkylation temperature in preparation for placing the reaction zone on-line for the alkylation reaction of iso-alkane and olefin feed. Both of the above-mentioned streams containing iso-alkane and hydrogen halide are produced as a side-cut stream from the isostripper fractionation zone in a combined amount of 1033 mass units per hour.

A bottom stream from the regenerate stripper and a bottom stream from the isostripper fractionation zone are combined to produce an alkylate product stream in an amount of 116 mass units per hour.

The foregoing description, drawing and illustrative embodiment clearly illustrate the advantages encompassed by the method of the present invention and the benefits to be afforded with the use thereof.

What is claimed:

1. An alkylation process for the production of motor fuel alkylate which process comprises:
   (a) reacting an alkene hydrocarbon, an alkane hydrocarbon and a hydrogen halide at alkylation conditions in a first catalytic reaction zone to produce a hydrocarbon stream comprising alkylate, unreacted alkane hydrocarbon and alkyl halide;
   (b) separating said hydrocarbon stream comprising alkylate, unreacted alkane hydrocarbon and alkyl halide in a separation zone to produce a hydrocarbon product stream comprising alkylate;
   (c) introducing an alkane hydrocarbon stream comprising n-alkane hydrocarbon and i-alkane hydrocarbon, and hydrogen halide into said separation zone to produce a stream comprising n-alkane hydrocarbon and a stream comprising i-alkane hydrocarbon and hydrogen halide;
   (d) passing at least a portion of said stream comprising i-alkane hydrocarbon and hydrogen halide produced in step (c) to step (a) to provide at least a portion of said alkane hydrocarbon;
   (e) passing n-alkane hydrocarbon to a second catalytic reaction zone to heat and flush said second catalytic reaction zone containing deactivated catalyst in preparation for regeneration of said deactivated catalyst;
   (f) withdrawing a stream comprising alkane hydrocarbon and alkyl halide from said separation zone and passing at least a portion of said stream comprising alkane hydrocarbon and alkyl halide, and hydrogen to a third catalytic reaction zone containing heated deactivated catalyst to thereby regenerate said heated deactivated catalyst and to produce an effluent stream comprising alkane hydrocarbon and hydrogen halide; and
   (g) passing at least a portion of said stream comprising i-alkane hydrocarbon and hydrogen halide produced in step (c) to cool and flush a fourth catalytic reaction zone containing newly regenerated catalyst.

2. The alkylation process of claim 1 wherein said alkylation conditions include a pressure in the range from about 100 to about 1500 psig and a temperature from about 32° F. (0° C.) to about 122° F. (50° C.) and an alkane to alkene olefin ratio from about 5 to about 20.

3. The alkylation process of claim 1 wherein said separation zone is operated at conditions which include a temperature from about 95° F. (35° C.) to about 464° F. (240° C.) and a pressure from about 100 psig (689 kPa gauge) to about 250 psig (1724 kPa gauge).

4. The alkylation process of claim 1 wherein said alkane contains from four to six carbon atoms.

5. The alkylation process of claim 1 wherein said alkene contains from 3 to 6 carbon atoms.

6. The alkylation process of claim 1 wherein said alkyl halides contain from 3 to about 5 carbon atoms.

7. The alkylation process of claim 1 wherein said hydrogen halide is selected from the group consisting of hydrogen fluoride and hydrogen chloride.

8. The alkylation process of claim 1 wherein said stream comprising n-alkane hydrocarbon produced in step (c) is purified in a rectification zone.

9. The alkylation process of claim 1 wherein said stream comprising alkane hydrocarbon and alkyl halide produced in step (f) is purified in a rectification zone.

10. The alkylation process of claim 1 wherein the regeneration conditions in step (f) include a temperature from about 250° F. (121° C.) to about 500° F. (260° C.).

11. An alkylation process for the production of motor fuel alkylate which process comprises:

(a) reacting an alkene hydrocarbon, an alkane hydrocarbon and a hydrogen halide at alkylation conditions in a first catalytic reaction zone to produce a hydrocarbon stream comprising alkylate, unreacted alkane hydrocarbon and alkyl halide;

(b) separating said hydrocarbon stream comprising alkylate, unreacted alkane hydrocarbon and alkyl halide in a first separation zone to produce a hydrocarbon product stream comprising alkylate;

(c) introducing an alkane hydrocarbon stream comprising n-alkane hydrocarbon and iso-alkane, and hydrogen halide into said first separation zone to produce a stream comprising n-alkane hydrocarbon and a stream comprising iso-alkane hydrocarbon and hydrogen halide;

(d) passing at least a portion of said stream comprising iso-alkane hydrocarbon and hydrogen halide produced in step (c) to step (a) to provide at least a portion of said alkane hydrocarbon;

(e) passing n-alkane hydrocarbon to a second catalytic reaction zone to heat and flush said second catalytic reaction zone containing deactivated catalyst in preparation for regeneration of said deactivated catalyst;

(f) withdrawing a stream comprising alkane hydrocarbon and alkyl halide from said first separation zone and passing at least a portion of said stream comprising alkane hydrocarbon and alkyl halide, and hydrogen to a third catalytic reaction zone containing heated deactivated catalyst to thereby regenerate said heated deactivated catalyst and to produce an effluent stream comprising alkane hydrocarbon and hydrogen halide;

(g) passing at least a portion of said effluent stream comprising alkane hydrocarbon and hydrogen halide from step (f) and at least a portion of the n-alkane effluent from step (e) to a second separation zone to produce a stream comprising n-alkane, and a vapor stream comprising hydrogen and hydrogen halide;

(h) passing at least a portion of said stream comprising n-alkane produced in step (g) to step (e) to provide at least a portion of said n-alkane hydrocarbon;

(i) passing at least a portion of said vapor stream comprising hydrogen and hydrogen halide produced in step (g) to step (f) to provide at least a portion of said hydrogen; and (j) passing at least a portion of said stream comprising iso-alkane hydrocarbon and hydrogen halide produced in step (c) to a fourth catalytic reaction zone containing freshly regenerated catalyst to thereby cool said freshly regenerated catalyst to alkylation temperature.

* * * * *